(12) United States Patent
Kasvikis et al.

(10) Patent No.: US 9,023,069 B2
(45) Date of Patent: May 5, 2015

(54) ATTACHABLE CLAMP FOR USE WITH SURGICAL INSTRUMENTS

(75) Inventors: Dino Kasvikis, Middletown, CT (US); Katelyn O'Donnell, East Haven, CT (US)

(73) Assignee: Covidien LP, Mansfield, MA (US)

( * ) Notice: Subject to any disclaimer, the term of this patent is extended or adjusted under 35 U.S.C. 154(b) by 730 days.

(21) Appl. No.: 12/467,324

(22) Filed: May 18, 2009

(65) Prior Publication Data

US 2010/0292716 A1 Nov. 18, 2010

(51) Int. Cl.
*A61B 17/08* (2006.01)
*A61B 17/068* (2006.01)
*A61B 1/00* (2006.01)
*A61B 17/072* (2006.01)
(Continued)

(52) U.S. Cl.
CPC .............. *A61B 17/068* (2013.01); *A61B 1/0014* (2013.01); *A61B 17/07207* (2013.01); *A61B 18/1445* (2013.01); *A61B 2017/00296* (2013.01); *A61B 2017/07221* (2013.01); *A61B 2017/2808* (2013.01); *A61B 2017/2923* (2013.01); *A61B 2017/2945* (2013.01); *A61B 2018/1432* (2013.01); *A61B 2018/1495* (2013.01)

(58) Field of Classification Search
CPC .. A61B 1/0014; A61B 17/068; A61B 17/072; A61B 17/07207; A61B 17/282; A61B 2017/07221; A61B 2017/00296; A61B 2017/2945; A61B 18/1445; A61B 2018/1432; A61B 2018/1495; A61B 2017/02808; A61B 2017/2923
USPC ......... 606/205–209, 167, 170, 171, 174, 142, 606/151, 157, 51, 52, 219, 221, 39–41, 83, 606/45, 220; 81/362, 355, 361; 294/106, 294/116; 227/180.1, 181.1, 175.1, 175.2, 227/19, 176.1–179.1, 175.3–175.4; 600/193, 175, 127, 112, 105, 106, 104, 600/221, 113, 153
See application file for complete search history.

(56) References Cited

U.S. PATENT DOCUMENTS

| | | |
|---|---|---|
| 804,229 A | 11/1905 | Hutchinson |
| 2,518,994 A | 8/1950 | Miller |

(Continued)

FOREIGN PATENT DOCUMENTS

| | | |
|---|---|---|
| EP | 0 246 870 A2 | 11/1987 |
| EP | 0 600 182 | 6/1994 |

(Continued)

OTHER PUBLICATIONS

European Search Report for EP 11250468.3 dated Aug. 10, 2011.
(Continued)

*Primary Examiner* — Jocelin Tanner

(57) ABSTRACT

An attachable clamp for use with a surgical instrument is disclosed. The attachable clamp comprises a body portion, a first jaw member, a second jaw member and an actuation mechanism. The body portion defines a longitudinal axis and has attachment members configured to attach to an elongate portion of a surgical instrument. Each of the first jaw member and second jaw member extends distally from the body portion. The actuation mechanism is disposed in mechanical cooperation with at least one of the first jaw member and the second jaw member. Actuation of the actuation mechanism moves at least one of the first and second jaw members between an approximated position and an open position with respect to the other jaw member.

32 Claims, 12 Drawing Sheets

(51) Int. Cl.
*A61B 18/14* (2006.01)
*A61B 17/00* (2006.01)
*A61B 17/28* (2006.01)
*A61B 17/29* (2006.01)

(56) References Cited

U.S. PATENT DOCUMENTS

| | | | |
|---|---|---|---|
| 3,017,637 A | 1/1962 | Sampson | |
| 3,834,021 A | 9/1974 | White et al. | |
| 4,299,224 A | 11/1981 | Noiles | |
| 4,605,001 A | 8/1986 | Rothfuss et al. | |
| 4,608,981 A | 9/1986 | Rothfuss et al. | |
| 4,617,928 A | 10/1986 | Alfranca | |
| 4,633,861 A | 1/1987 | Chow et al. | |
| 4,633,874 A | 1/1987 | Chow et al. | |
| 4,655,216 A | 4/1987 | Tischer | |
| 4,733,662 A * | 3/1988 | DeSatnick et al. | 606/171 |
| 4,881,544 A | 11/1989 | Green et al. | |
| 4,881,545 A | 11/1989 | Isaacs et al. | |
| 4,967,949 A | 11/1990 | Sandhaus | |
| 4,991,764 A | 2/1991 | Mericle | |
| 5,040,715 A | 8/1991 | Green et al. | |
| 5,049,152 A | 9/1991 | Simon et al. | |
| 5,067,958 A | 11/1991 | Sandhaus | |
| 5,071,430 A | 12/1991 | De Salis et al. | |
| 5,147,357 A | 9/1992 | Rose et al. | |
| 5,147,373 A | 9/1992 | Ferzli | |
| 5,152,780 A | 10/1992 | Honkanen et al. | |
| 5,156,608 A | 10/1992 | Troidl et al. | |
| 5,171,257 A | 12/1992 | Ferzli | |
| 5,201,739 A | 4/1993 | Semm | |
| 5,201,743 A | 4/1993 | Haber et al. | |
| 5,201,759 A | 4/1993 | Ferzli | |
| 5,217,460 A | 6/1993 | Knoepfler | |
| 5,219,357 A | 6/1993 | Honkanen et al. | |
| 5,275,613 A | 1/1994 | Haber et al. | |
| 5,275,614 A | 1/1994 | Haber et al. | |
| 5,281,235 A | 1/1994 | Haber et al. | |
| 5,282,806 A | 2/1994 | Haber et al. | |
| 5,318,221 A | 6/1994 | Green et al. | |
| 5,336,232 A * | 8/1994 | Green et al. | 606/151 |
| 5,337,937 A | 8/1994 | Remiszewshi et al. | |
| 5,358,506 A | 10/1994 | Green et al. | |
| 5,366,134 A | 11/1994 | Green et al. | |
| 5,366,477 A | 11/1994 | LeMarie, III et al. | |
| 5,383,886 A * | 1/1995 | Kensey et al. | 606/185 |
| 5,389,098 A | 2/1995 | Tsuruta et al. | |
| 5,395,367 A * | 3/1995 | Wilk | 606/1 |
| 5,470,008 A | 11/1995 | Rodak | |
| 5,496,347 A | 3/1996 | Hashguchi et al. | |
| 5,507,772 A | 4/1996 | Shutt et al. | |
| 5,507,773 A | 4/1996 | Huitema et al. | |
| 5,540,375 A | 7/1996 | Bolanos et al. | |
| 5,562,700 A | 10/1996 | Huitema et al. | |
| 5,562,702 A | 10/1996 | Huitema et al. | |
| 5,582,617 A | 12/1996 | Klieman et al. | |
| 5,590,570 A | 1/1997 | LeMarie, III et al. | |
| 5,618,304 A | 4/1997 | Hart et al. | |
| 5,653,721 A | 8/1997 | Knodel et al. | |
| 5,665,050 A | 9/1997 | Benecke | |
| 5,676,674 A | 10/1997 | Bolanos et al. | |
| 5,695,522 A | 12/1997 | LeMarie, III et al. | |
| 5,700,276 A | 12/1997 | Benecke | |
| 5,702,048 A | 12/1997 | Eberlin | |
| 5,749,893 A | 5/1998 | Vidal et al. | |
| 5,776,146 A | 7/1998 | Sackier et al. | |
| 5,810,877 A | 9/1998 | Roth et al. | |
| 5,816,471 A | 10/1998 | Plyley et al. | |
| 5,827,323 A | 10/1998 | Klieman et al. | |
| 5,849,022 A | 12/1998 | Sakashita et al. | |
| 5,868,786 A | 2/1999 | DiFrancesco | |
| 5,919,206 A | 7/1999 | Gengler et al. | |
| 5,928,264 A | 7/1999 | Sugarbaker et al. | |
| 5,993,464 A | 11/1999 | Knodel | |
| 6,015,426 A | 1/2000 | Griffiths | |
| 6,019,780 A | 2/2000 | Lombardo et al. | |
| RE36,666 E | 4/2000 | Hankanen et al. | |
| 6,063,103 A | 5/2000 | Hashiguchi | |
| 6,228,097 B1 * | 5/2001 | Levinson et al. | 606/142 |
| 6,241,139 B1 * | 6/2001 | Milliman et al. | 227/175.1 |
| 6,270,508 B1 | 8/2001 | Klieman et al. | |
| 6,352,503 B1 * | 3/2002 | Matsui et al. | 600/104 |
| 6,358,267 B1 | 3/2002 | Murakami et al. | |
| 6,391,043 B1 | 5/2002 | Moll et al. | |
| 6,599,309 B1 | 7/2003 | Gilman | |
| 6,673,092 B1 * | 1/2004 | Bacher | 606/205 |
| 6,755,338 B2 | 6/2004 | Hahnen et al. | |
| 6,830,174 B2 | 12/2004 | Hillstead et al. | |
| 6,835,199 B2 | 12/2004 | McGuckin, Jr. et al. | |
| 7,011,657 B2 | 3/2006 | Truckai et al. | |
| 7,108,703 B2 | 9/2006 | Danitz et al. | |
| 7,121,446 B2 | 10/2006 | Arad et al. | |
| 7,208,005 B2 | 4/2007 | Frecker et al. | |
| 7,211,099 B2 | 5/2007 | Lang et al | |
| 7,223,273 B2 | 5/2007 | Manzo | |
| 7,316,703 B2 | 1/2008 | Suzuki | |
| 7,328,829 B2 | 2/2008 | Arad et al. | |
| 7,404,508 B2 | 7/2008 | Smith et al. | |
| 7,434,717 B2 | 10/2008 | Shelton, IV et al. | |
| 7,464,849 B2 | 12/2008 | Shelton, IV et al. | |
| 7,543,730 B1 | 6/2009 | Marczyk | |
| 2002/0065523 A1 | 5/2002 | McAlister | |
| 2002/0143346 A1 * | 10/2002 | McGuckin et al. | 606/139 |
| 2004/0084497 A1 * | 5/2004 | Aranyi | 227/1 |
| 2004/0106852 A1 * | 6/2004 | Windheuser et al. | 600/125 |
| 2004/0222268 A1 * | 11/2004 | Bilotti et al. | 227/180.1 |
| 2005/0228224 A1 * | 10/2005 | Okada et al. | 600/104 |
| 2005/0234297 A1 * | 10/2005 | Devierre et al. | 600/153 |
| 2006/0163312 A1 | 7/2006 | Viola et al. | |
| 2007/0095877 A1 | 5/2007 | Racenet et al. | |
| 2007/0187456 A1 | 8/2007 | Viola et al. | |
| 2007/0244515 A1 * | 10/2007 | Fanous | 606/205 |
| 2007/0265640 A1 | 11/2007 | Kortenbach et al. | |
| 2008/0048002 A1 | 2/2008 | Smith et al. | |
| 2008/0078800 A1 | 4/2008 | Hess et al. | |
| 2008/0154091 A1 * | 6/2008 | Dejima et al. | 600/104 |
| 2008/0169328 A1 | 7/2008 | Shelton | |
| 2009/0125002 A1 * | 5/2009 | Totz | 604/528 |
| 2010/0072258 A1 | 3/2010 | Farascioni et al. | |
| 2010/0213238 A1 | 8/2010 | Farascioni et al. | |

FOREIGN PATENT DOCUMENTS

| | | |
|---|---|---|
| EP | 1 550 412 A2 | 7/2005 |
| EP | 1621139 A | 2/2006 |
| EP | 1 875 868 A1 | 1/2008 |
| EP | 1908414 A | 4/2008 |
| EP | 1 935 354 A2 | 6/2008 |
| EP | 1 550 411 B1 | 7/2009 |
| EP | 2 130 501 A1 | 12/2009 |
| GB | 2029754 | 3/1980 |
| WO | WO 02/30296 | 4/2002 |
| WO | WO 2006/055385 | 5/2006 |

OTHER PUBLICATIONS

European Search Report for corresponding EP 10 25 0934, date of completion is Aug. 19, 2010 (3 pages).
European Search Report EP 09251240 dated Oct. 5, 2009. (8 pages).
European Search Report for EP 11178544 dated Sep. 29, 2011.
European Search Report for EP 11193444.4-1269 date of completion is Jan. 24, 2012 (3 pages).
European Search Report for Application No. 09251420.7 dated Sep. 7, 2009. (2 pages).
European Search Report for EP 09252246.5-1269 date of completion is Nov. 24, 2009 (3 pages).

* cited by examiner

ATTACHABLE CLAMP FOR USE WITH SURGICAL INSTRUMENTS

BACKGROUND

1. Technical Field

The present disclosure relates generally to instruments for surgically joining tissue and, more specifically, to an accessory for grasping and/or clamping tissue, for use with a surgical instrument for joining and/or cutting tissue.

2. Background of Related Art

Various types of surgical instruments used to surgically join tissue are known in the art, and are commonly used, for example, for closure of tissue or organs in transection, resection, anastomoses, for occlusion of organs in thoracic and abdominal procedures, and for electrosurgically fusing or sealing tissue.

One example of such a surgical instrument is a surgical stapling instrument, which may include an anvil assembly, a cartridge assembly for supporting an array of surgical staples, an approximation mechanism for approximating the cartridge and anvil assemblies, and a firing mechanism for ejecting the surgical staples from the cartridge assembly.

Using a surgical stapling instrument, it is common for a surgeon to approximate the anvil and cartridge members. Next, the surgeon can fire the instrument to emplace staples in tissue. Additionally, the surgeon may use the same instrument or a separate instrument to cut the tissue adjacent or between the row(s) of staples.

Other examples of a surgical instrument of the present disclosure include electrosurgical (e.g., monopolar and bipolar) forceps. Electrosurgical forceps utilize both mechanical clamping action and electrical energy to affect hemostasis by heating the tissue and blood vessels to coagulate, cauterize and/or seal tissue.

In certain procedures, some surgeons wash out the inside of an organ prior to cutting and stapling (or otherwise joining) the tissue. A clamp may be used to define an area to be washed out.

SUMMARY

The present disclosure relates to an attachable clamp for use with a surgical instrument. The attachable clamp comprises a body portion, a first jaw member, a second jaw member and an actuation mechanism. The body portion defines a longitudinal axis and has attachment members configured to attach to an elongate portion of a surgical instrument. Each of the first jaw member and second jaw member extends distally from the body portion. The actuation mechanism is disposed in mechanical cooperation with at least one of the first jaw member and the second jaw member. Actuation of the actuation mechanism moves at least one of the first and second jaw members between an approximated position and an open position with respect to the other jaw member.

The attachable clamp has attachment members configured to removably attach to the body portion and to removably attach to the elongate portion of the surgical instrument, in certain embodiments.

In certain embodiments, the first jaw member and the second jaw member may correspond to jaws of the surgical instrument in shape and orientation.

Each of the first jaw member and the second jaw member may be curved with respect to the longitudinal axis and include a concave and a convex side. The jaws of the surgical instrument may be curved, and they may have a convex side and a concave side. In certain embodiments, the convex side of the first jaw member and the second jaw member is disposed adjacent the jaws of the surgical instrument, and in other embodiments, the concave side of the first jaw member and the second jaw member is disposed adjacent the jaws of the surgical instrument.

The actuation mechanism can include a first cam plate disposed in mechanical cooperation with the first jaw member and disposed in mechanical cooperation with a rod. Translation of the rod causes the first jaw member to move upwardly. The translation of the rod in a first direction causes the first jaw member to move upwardly toward the open position. The rod is desirably biased toward a position so that the first jaw member tends to move toward the approximated position.

The actuation mechanism, in certain embodiments, further comprises a second cam plate disposed in mechanical cooperation with the second jaw member and disposed in mechanical cooperation with the rod. Translation of the rod causes the second jaw member to move downwardly. The translation of the rod in a first direction causes the second jaw member to move downwardly toward the open position.

In certain embodiments, the first jaw member and second jaw member are substantially parallel to one another when the jaw members are in the open and approximated positions. The first jaw member may be stationary with respect to the body portion.

The actuation mechanism may include a knob and a slide member, wherein rotation of the knob causes the second jaw member to pivot towards the first jaw member. The knob can include a plurality of teeth that are configured to engage a plurality of teeth on the slide member.

In another aspect, the present disclosure also relates to a method of surgically joining tissue. The method comprises the step of providing a surgical instrument including a handle portion, an endoscopic portion and a pair of jaw members. The endoscopic portion extends distally from the handle portion. The pair of jaw members is disposed adjacent a distal end of the endoscopic portion. At least one of the jaw members is movable with respect to the other between an open position and an approximated position for engaging body tissue therebetween. The method also comprises the step of providing an attachable clamp configured to be attached to the surgical instrument. The attachable clamp includes a body portion, a first jaw member, a second jaw member, and an actuation mechanism. The body portion defines a longitudinal axis. The first and second jaw members extend distally from the body portion. The actuation mechanism is disposed in mechanical cooperation with at least one of the first jaw member and the second jaw member. At least one jaw member of the attachable clamp is independently movable with respect to the jaw members of the surgical instrument. The method also includes the steps of moving at least one jaw member of the attachable clamp from an open position towards an approximated position to engage body tissue, moving at least one of the jaw members of the surgical instrument with respect to the other from an open position towards an approximated position to engage body tissue, and actuating the jaw members of the surgical instrument to join tissue.

In a further aspect of the present disclosure, an attachable clamp for use with a surgical instrument comprises: a body portion defining a longitudinal axis and having attachment members configured to attach to a surgical instrument; a first jaw member extending distally from the body portion; and a second jaw member extending distally from the body portion. The attachable clamp further includes an actuation mechanism disposed in mechanical cooperation with at least one of the first jaw member and the second jaw member, wherein actuation of the actuation mechanism moves at least one of the first and second jaw members between an approximated position for clamping tissue and an open position with respect to the other jaw member. The actuation mechanism holds the jaw members in the approximated position and has an actuator graspable by a user for releasing the actuation mechanism.

In certain embodiments, the attachable clamp has attachment members that are configured to removably attach to the elongate portion of the surgical instrument. The first jaw member and second jaw member of the attachable clamp desirably correspond to jaws of the surgical instrument in shape and orientation.

The actuation mechanism may include a first cam plate disposed in mechanical cooperation with the first jaw member and disposed in mechanical cooperation with a rod, and wherein translation of the rod causes the first jaw member to move upwardly toward the open position. The actuation mechanism desirably biases the first jaw member and the second jaw member toward the approximated position.

The first jaw member and the second jaw member are substantially parallel to one another when the jaw members are in the open and approximated positions, in certain embodiments. The first jaw member may be stationary with respect to the body portion.

The actuation mechanism includes a slide member having teeth, in certain embodiments of the present disclosure. The actuation mechanism may includes locking member that engages the teeth of the slide member. The teeth are configured to allow the slide member to slide with respect to the locking member in a first direction and configured to engage the locking member to move the slide member in a second direction.

In certain embodiments, the actuation mechanism includes a detent configured to allow the slide member to slide with respect to the detent in a first direction and configured to engage the slide member to move the slide member in a second direction.

BRIEF DESCRIPTION OF FIGURES

Various embodiments of the presently disclosed surgical instrument are disclosed herein with reference to the drawings, wherein.

DETAILED DESCRIPTION

Figure 1A:
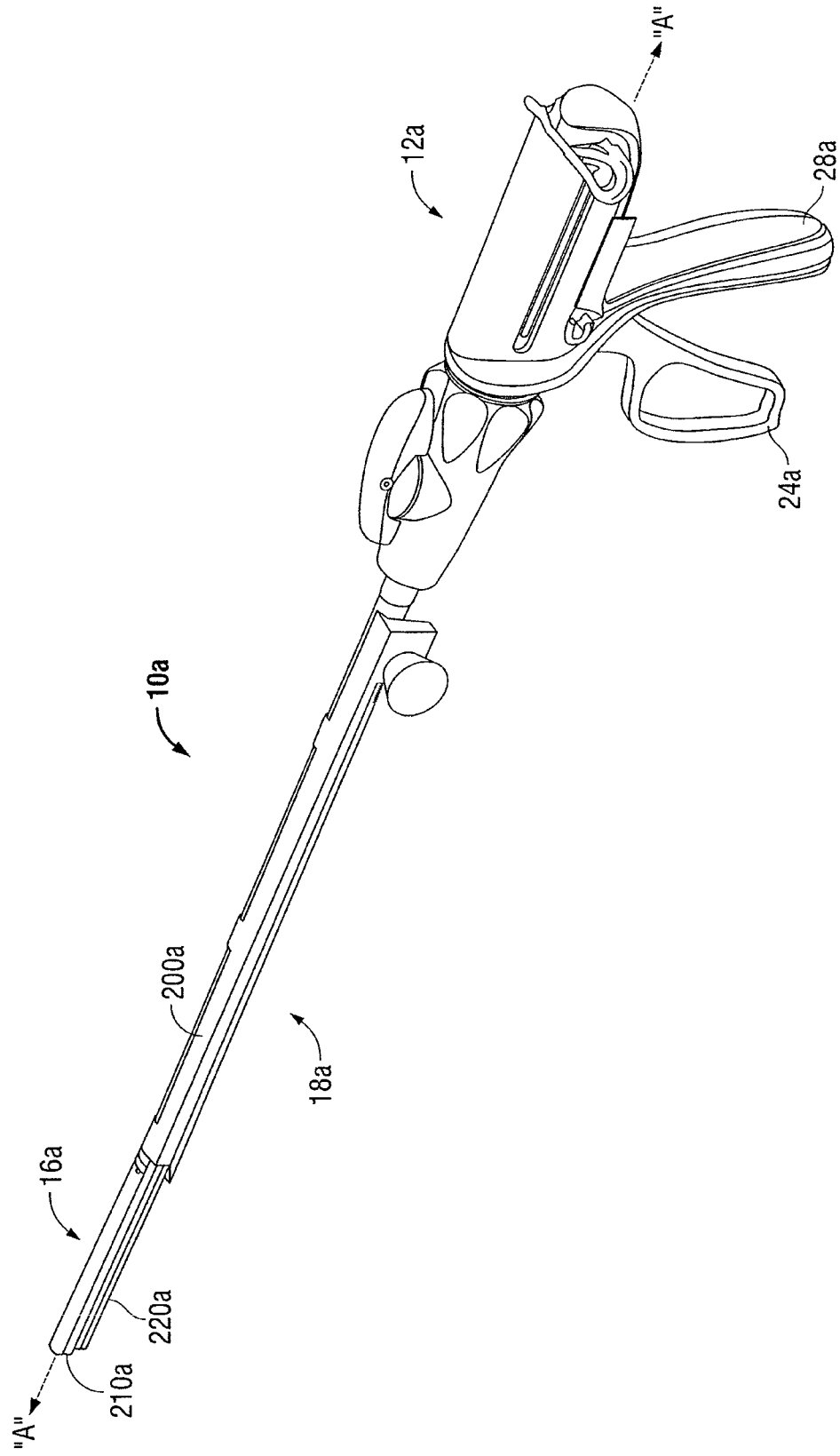
FIG. 1A is a perspective view of a linear surgical stapling instrument including an attachable clamp in accordance with the present disclosure.

Embodiments of the presently disclosed clamp for use with a surgical instrument are described in detail with reference to the drawings, wherein like reference numerals designate corresponding elements in each of the several views. In the description that follows, the term "proximal" refers to the end or portion of the clamp closer to the clinician, whereas the term "distal" refers to the end or portion of the clamp farther away from the clinician.

Figure 1B:
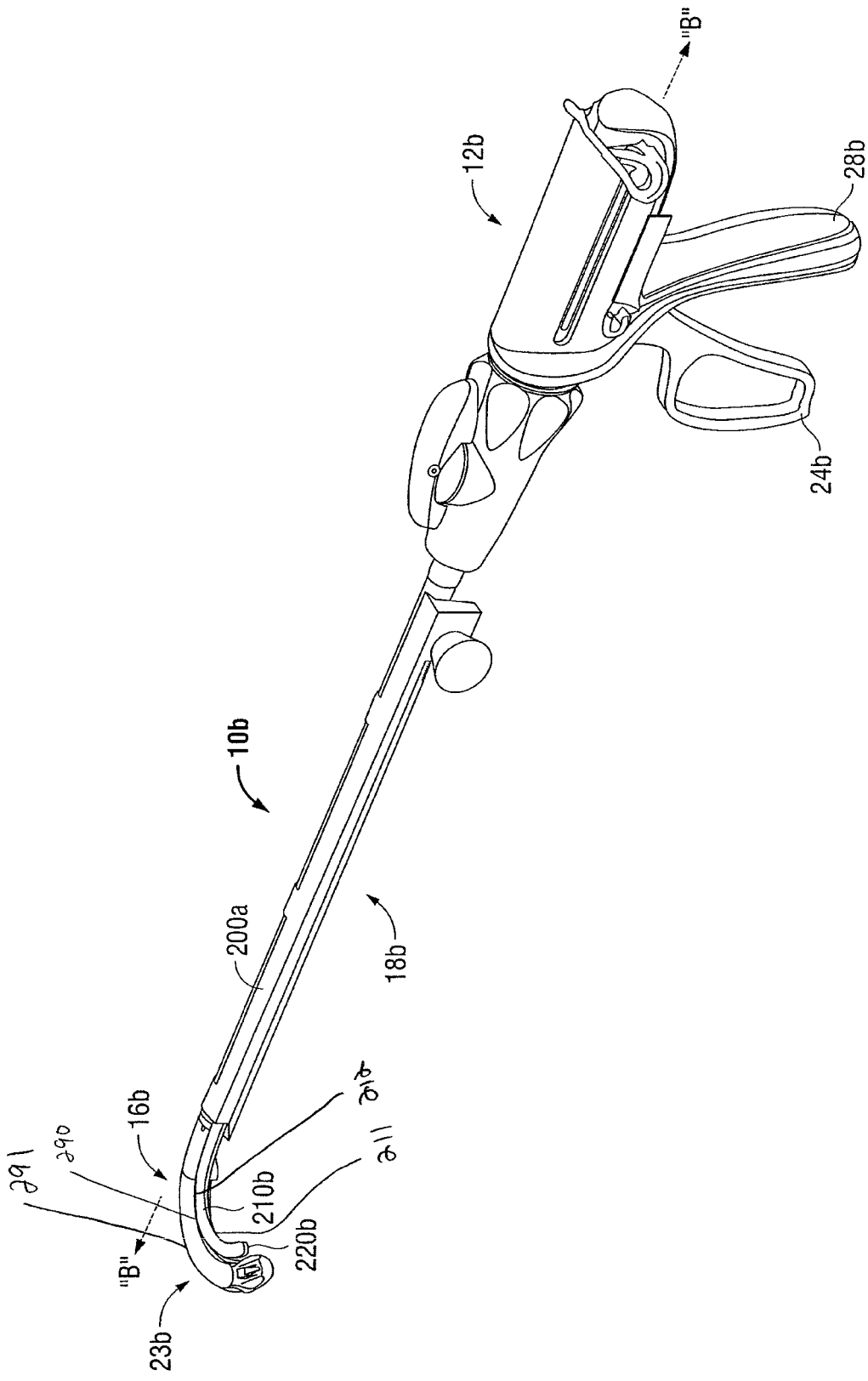
FIG. 1B is a perspective view of an surgical stapling instrument having curved jaw members and including an attachable clamp in accordance with the present disclosure.
Figure 1C:
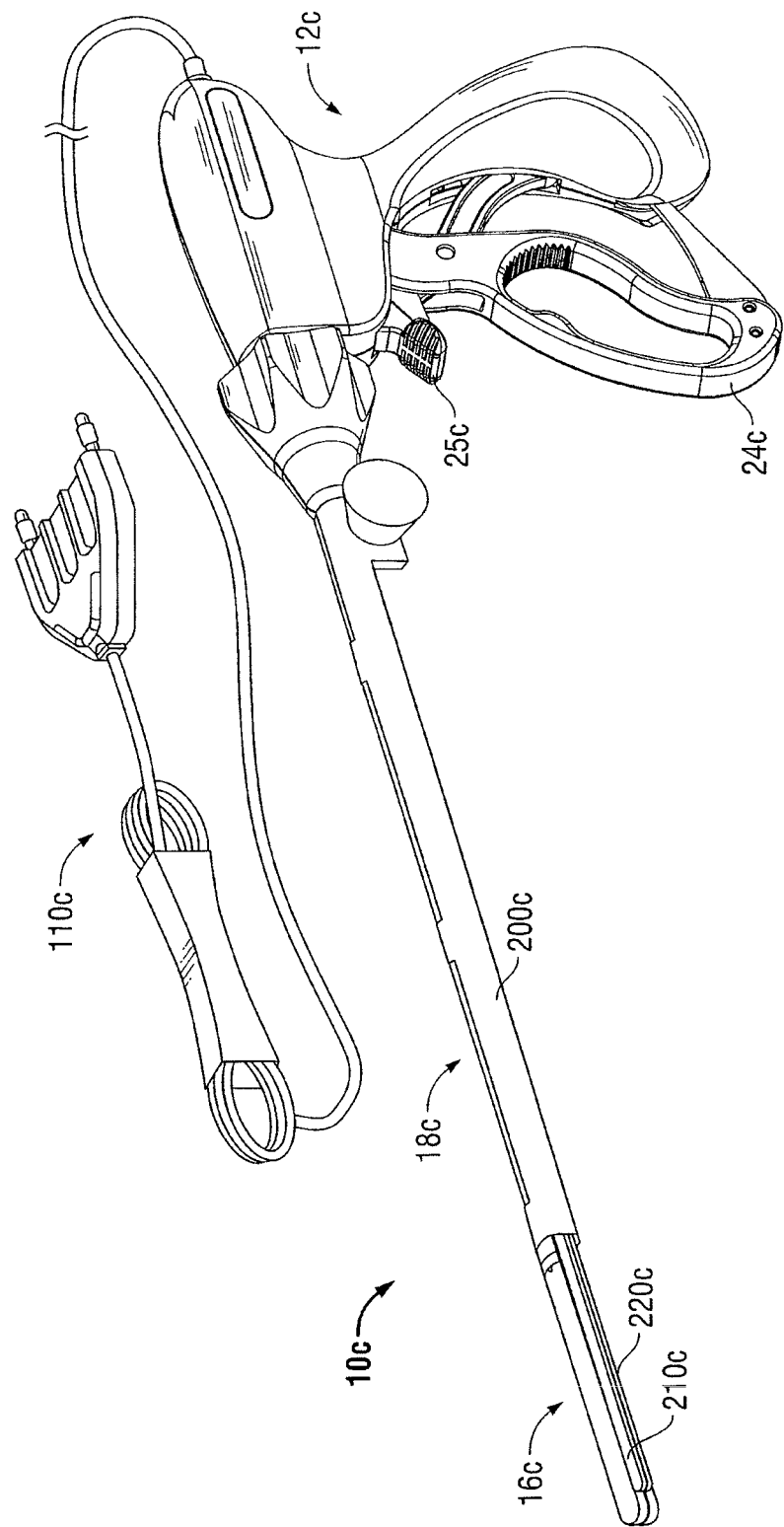
FIG. 1C is a perspective view of a vessel sealing instrument including an attachable clamp in accordance with the present disclosure.
Figure 2:
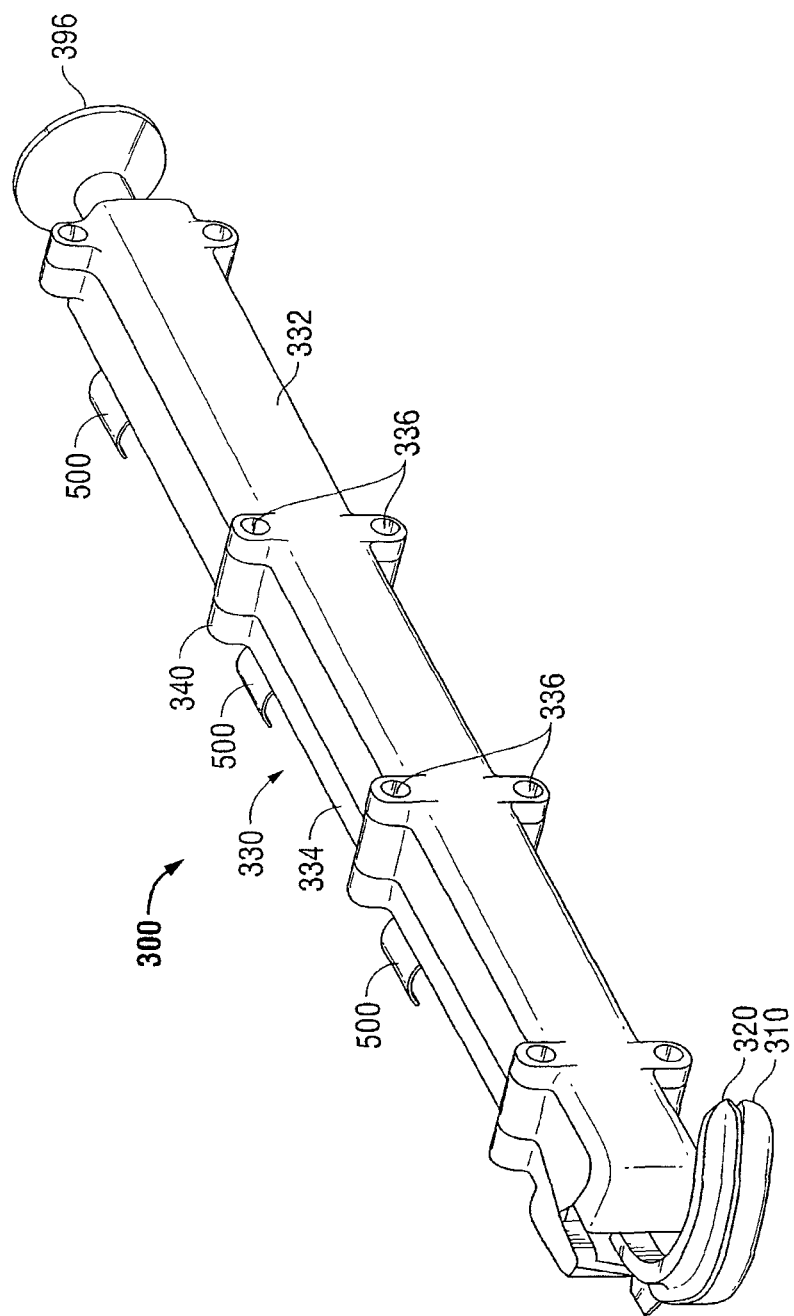
FIGS. 2-4 are perspective views of an accessory according to an embodiment of the present disclosure, shown at various stages of operation, for use with the surgical instruments of FIGS. 1A and 1B.

Referring initially to FIGS. 1A-1C, various surgical instruments are shown in accordance with the present disclosure. In particular, FIG. 1A discloses a linear surgical stapling instrument 10a, FIG. 1B discloses a surgical stapling instrument 10b having curved jaws 23b, and FIG. 1C discloses a vessel sealing instrument 10c. As discussed herein, surgical instruments 10a-10c are collectively referred to as reference number 10.

With reference to FIG. 1A, linear surgical stapling apparatus 10a includes a handle assembly 12a near a proximal end, an end effector 16a near a distal end and an elongate portion 18a therebetween. The end effector 16a may be positioned within a body cavity to engage tissue at a surgical site while handle assembly 12a is manipulatable by a surgeon from outside the body cavity to control the movement and operation of the end effector 16a. Elongate portion 18a defines a longitudinal axis A-A.

End effector 16a includes a cartridge assembly, which houses a plurality of staples arranged in linear rows, and an anvil assembly for forming the staples. At least one of the cartridge assembly and the anvil assembly is movable with respect to the other between an open position wherein the cartridge assembly is substantially spaced from the anvil assembly and an approximated position where the cartridge assembly and the anvil assembly are closer together. A pivotable trigger 24a of the handle assembly 12a is movable through an actuation stroke or strokes relative to a stationary grip member 28a to move the cartridge assembly in relation to the anvil assembly between the open position and the approximated position and to eject the staples from the cartridge assembly. Further details of a linear surgical stapling instrument are described in detail in commonly-owned U.S. Pat. No. 6,953,139 to Milliman et al., the entire contents of which are hereby incorporated by reference herein. The cartridge assembly may include a replaceable cartridge body that houses the staples and staple pushers. Alternatively, the end effector 16a may form part of a separate, replaceable loading unit that is attachable to the elongate portion 18a of the stapling apparatus 10a. The loading unit includes an elongate body that is configured to attach to the elongate portion 18a through a detent, bayonet or similar attachment feature. The end effector 16a may be pivotably attached to the elongate body, in the example of a loading unit, or the elongate portion 18a, in the example of a stapling apparatus where a replaceable cartridge body is used.

With reference to FIG. 1B, surgical stapling apparatus 10b having curved jaws 23b is shown. Surgical stapling apparatus 10b and linear surgical stapling apparatus 10a share various common features, including handle assembly 12b, end effector 16b, and elongate portion 18b, as discussed above. The surgical stapling apparatus 10b includes curved jaws 23b. That is, surgical stapling apparatus 10b includes an end effector 16b having a cartridge assembly and an anvil assembly (collectively "jaws 23b"), that are each curved with respect to a longitudinal axis B-B, defined by elongated portion 18b. It is envisioned that curved jaws 23b facilitate performing certain types of surgical procedures. The curved jaws are arranged to facilitate use in procedures involving limited access to the targeted surgical site. For example, curved jaws 23b, as compared to linear jaws (such as the jaws illustrated in FIG. 1A), may help facilitate access to lower pelvis regions, e.g., during lower anterior resection ("LAR"). Additionally, the inclusion of curved jaws 23b may allow increased visualization to a surgical site and may also allow more room for a surgeon to manipulate target tissue of the jaws 23b themselves with his or her hand. The cartridge assembly may include a replaceable cartridge body that houses the staples and staple pushers. Alternatively, the end effector 16b may form part of a separate, replaceable loading unit that is attachable to the elongate portion 18b of the stapling apparatus 10b. The loading unit includes an elongate body that is configured to attach to the elongate portion 18b through a detent, bayonet or similar attachment feature. The end effector 16b may be pivotably attached to the elongate body, in the example of a loading unit, or the elongate portion 18b, in the example of a stapling apparatus where a replaceable cartridge body is used.

Referring now to FIG. 1C, a vessel sealing instrument 10c may also embody various aspects of the present disclosure. Vessel sealing instrument 10c includes a connector assembly 110c for connection to a source of electrosurgical energy (not shown). Vessel sealing instrument 10c includes a handle assembly 12c near a proximal end, an end effector 16c near a distal end and an elongate portion 18c therebetween. The end effector 16c may be positioned within a body cavity to engage tissue at a surgical site while handle assembly 12c is manipulatable by a surgeon from outside the body cavity to control the movement and operation of the end effector 16c. Handle assembly 12c includes a movable handle 24c, which may be manipulated to open and close the jaws of end effector 16c, and a trigger 25c, which may be manipulated to initiate an electrosurgical current. Further details of a vessel sealing instrument are described in U.S. Pat. No. 7,083,618, which is incorporated herein in its entirety by reference.

An accessory for grasping and/or clamping tissue is shown in FIGS. 1A-1C as attachable clamp 200. FIG. 1A illustrates an attachable clamp 200a engaged with linear surgical stapling instrument 10a. In this embodiment, clamp 200a includes a first linear jaw member 210a and a second linear jaw member 220a. FIG. 1B illustrates an attachable clamp 200b engaged with surgical stapling instrument 10b having curved jaws. In this embodiment, clamp 200b includes a first curved jaw member 210b and a second curved jaw member 220b. FIG. 1C illustrates an attachable clamp 200c engaged with vessel sealing instrument 10c. In this embodiment, clamp 200c includes a first linear jaw member 210c and a second linear jaw member 220c. While FIGS. 1A-1C illustrate one type of an attachable clamp 200, other embodiments of attachable clamps are described herein (as reference numbers 300 and 400) and each embodiment thereof is configured for use with surgical instruments 10.

Referring back to FIG. 1B, the curvature of jaw members 210b, 220b of attachable clamp 200b is shown as being approximately equal to, or corresponding to, the curvature of jaws 23b of surgical stapling instrument 10b. While not explicitly shown, it is envisioned that the curvature of jaw members 210b, 220b of attachable clamp 200b is either greater than or less than the curvature of jaws 23b of surgical stapling instrument 10b. It is also envisioned that the curvature of first jaw member 210b is different from the curvature of second jaw member 220b. In the surgical stapling instrument shown in FIG. 1B, jaws 23b have a concave side 290 and a convex side 291. Additionally, jaw members 210b, 220b of attachable clamp 200b are shown having a concave side 211 and a convex side 212. However, other curved shapes can be used for jaws 23b and/or jaw members 210b, 220b.

Referring now to FIGS. 2-5, various details of an attachable clamp in accordance with an embodiment of the present disclosure are illustrated. In this embodiment, attachable clamp is generally referred to as reference number 300. Attachable clamp 300 includes a first jaw member 310 and a second jaw member 320 that extend distally from an elongated body portion 330. Elongated body portion 330 is shown being comprised of a first body half 332 and a second body half 334 (first body half 332 is omitted in FIG. 4). A plurality of apertures 336 is disposed on each of the first body half 332 and the second body half 334 and may be used (e.g., in combination with appropriate fasteners such as screws, rivets snap-fit connectors, ultrasonic welds, etc.) to facilitate the attachment of each body half 332, 334 to one another and to a frame 340.

Figure 5:
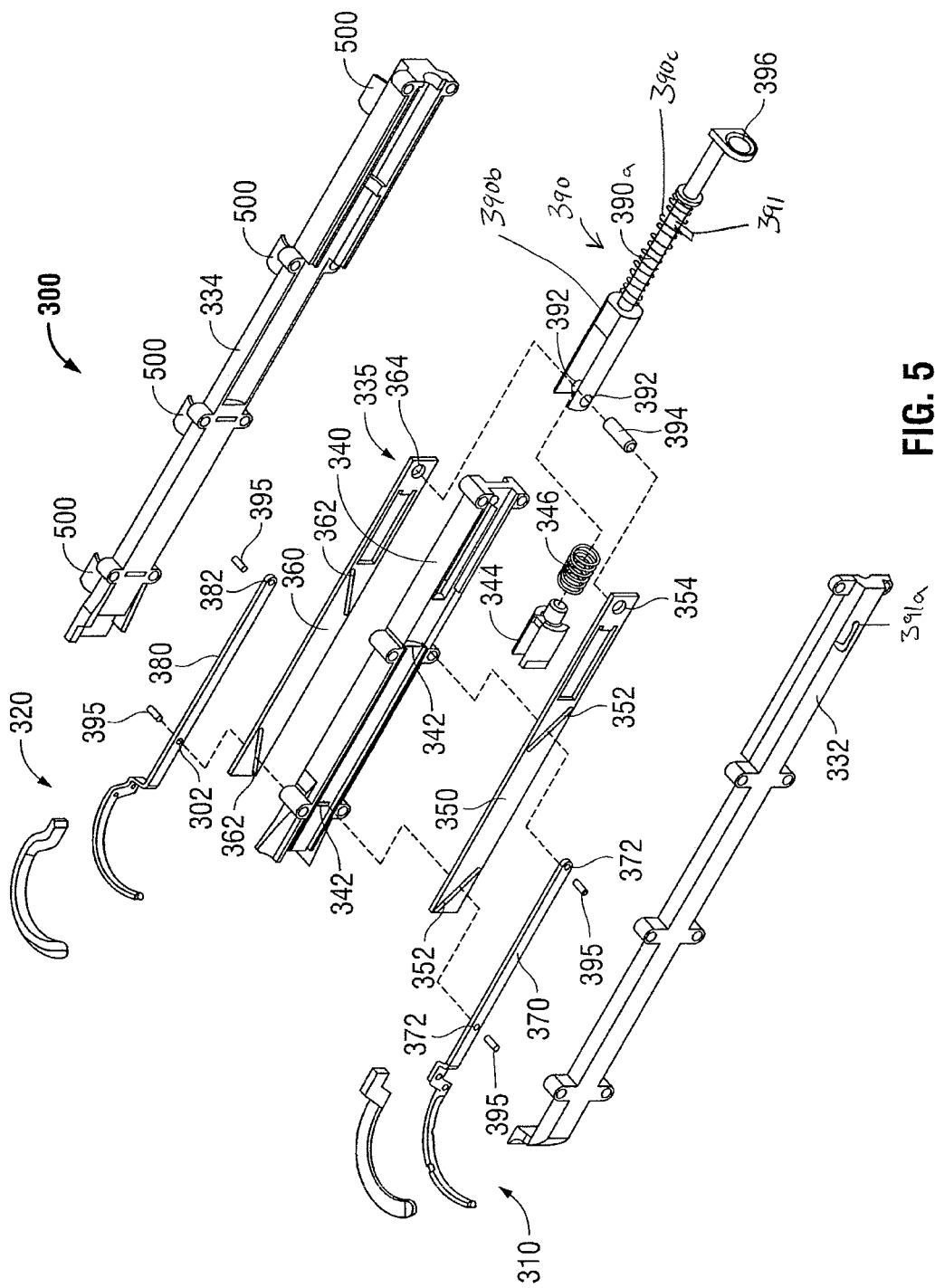
FIG. 5 is an exploded views of the accessory according to the embodiment shown in FIGS. 2-4, illustrating a closing mechanism for use with a clamp.

With reference to the assembly view illustrated in FIG. 5, clamp attachment 300 also includes an actuation mechanism 335 including a frame 240, a first cam plate 350, a second cam plate 360, a lower arm 370, an upper arm 380, and a rod 390. The lower arm 370 has the first jaw member 310, which may be attached thereto or integrally formed therewith. The first jaw member 310 desirably includes a tissue contact surface 310a. The upper arm 380 has the second jaw member 320, which may be attached thereto or formed integrally formed therewith. The second jaw member includes a tissue contact surface 320a. Frame 340 is disposed between and is relatively stationary with respect to first body half 332 and second body half 334, and includes vertically disposed slots 342 (two slots are shown) extending therethrough. At least a portion of slots 342 is configured for substantial alignment with at least a portion of corresponding diagonally disposed slots 352 in the first cam plate 350 and diagonally disposed slots 362 in the second cam plate 360. Additionally, at least a portion of slots 342 is configured to substantially align with corresponding apertures 372, 382 in respective lower arm 370 and upper arm 380. As discussed in more detail below, a plurality of pins 395 is used to movably secure first cam plate 350 with respect to frame 340 and lower arm 370 via slots 352, 342, and apertures 372, respectively. Additionally, a plurality of pins 395 (either the same pins or an additional set of pins) is used to movably secure second cam plate 360 with respect to frame 340 and upper arm 380 via slots 362, 342 and apertures 382, respectively.

The first cam plate 350 includes an aperture 354 disposed adjacent a proximal portion thereof and the second cam plate 360 includes an aperture 364 disposed adjacent a proximal portion thereof. Additionally, the rod 390 includes a pair of apertures 392 disposed adjacent a distal portion thereof. A pin 394 extends through apertures 354, 392 and 364 to secure rod 390 to cam plates 350, 360.

With continued reference to FIG. 5, the frame 340 includes a spring plug 344 disposed in mechanical cooperation therewith. Spring plug 344 is configured to engage a distal portion of a biasing member 346 (e.g., a helical spring). A proximal portion of biasing member 346 is configured to engage the distal portion of rod 390. Accordingly, the biasing member 346 is configured to bias rod 390 proximally with respect to frame 340.

In use, to operate attachable clamp 300, a user distally pushes a knob 396 of rod 390 against the bias of biasing member 346 to move the jaw members 310 and 320 towards the open position. More particularly, since the rod 390 is pinned to first cam plate 350 and second cam plate 360, distal movement of the rod 390 causes distal translation of cam plates 350 and 360. With initial regard to the first jaw member 310, as the first cam plate 350 translates distally, the pinned relationship between the lower arm 370, the slots 352 (which slope upward as they extend distally), and the vertical slots 342, causes the lower arm 370 to move downward with respect to frame 340. That is, when the first cam plate 350 is moved distally, the pins 395 travel downwardly and proximally with respect to slots 352. Moreover, the vertical slots 342 limit the motion of the lower arm 370 such that the lower arm 370 only moves downwardly (and not proximally) with respect to frame 340.

Correspondingly, with regard to the second jaw member 320, as the second cam plate 360 translates distally, the pinned relationship between the upper arm 380, the slots 362 (which slope downward as they extend distally), and the vertical slots 342, causes the upper arm 380 to move upward with respect to frame 340. That is, when the second cam plate 360 is moved distally, the pins 395 travel upwardly and proximally with respect to slots 362. Moreover, the vertical slots 342 limit the motion of the upper arm 380 such that the upper arm 380 only moves upwardly (and not proximally) with respect to frame 340.

Figure 3:
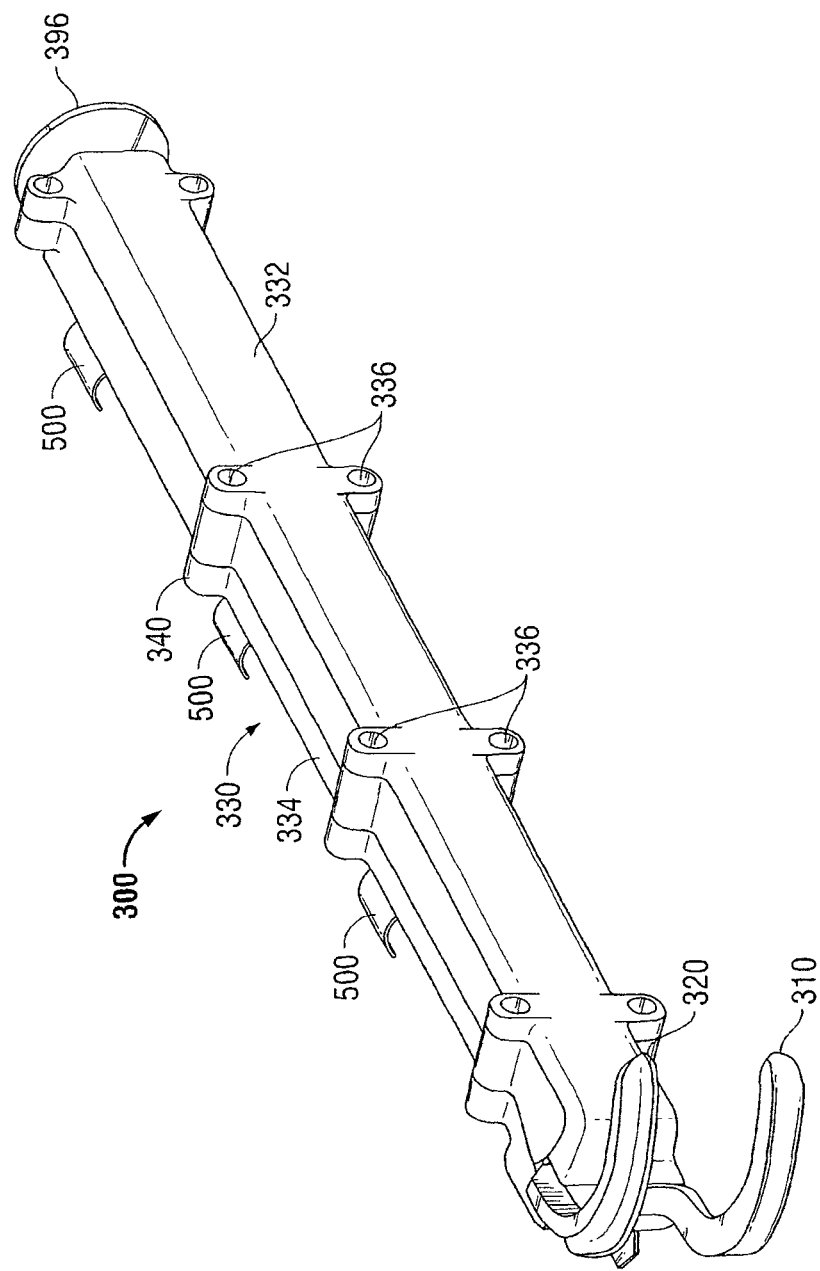
Figure 4:
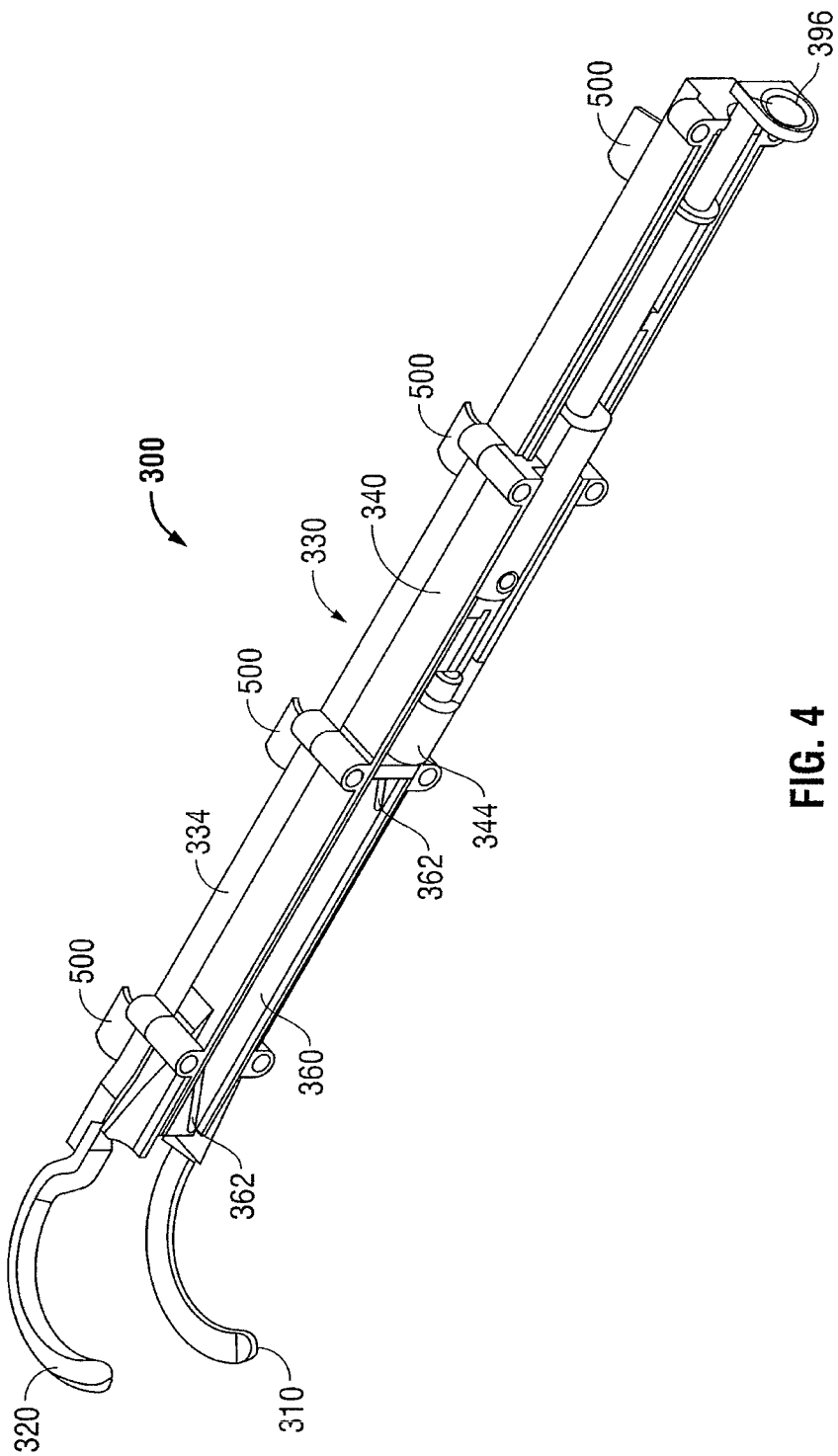

As can be appreciated with reference to FIGS. 2-5 and with reference to the discussion hereinabove, proximal movement of the knob 396 (i.e., in the direction provided by the bias of biasing member 346) causes first cam plate 350 and second cam plate 360 to move proximally. Proximal movement of first cam plate 350 causes lower arm 370 to move upward with respect to frame 340. Proximal movement of second cam plate 360 causes upper arm 380 to move downward with respect to frame 340. Thus, the jaw members 310, 320 move between a first substantially parallel approximated position (FIG. 2) and a second substantially parallel open position (FIG. 3). Additionally, as described above, the jaw members 310, 320 of attachable clamp 300 are biased towards their approximated positions. As can be appreciated, a particular biasing member 346 may be selected (e.g., having a particular spring constant) to provide a desired about of closing force.

It is also envisioned that attachable clamp 300 includes structure to releasably lock jaw members 310, 320 in an open position. In such an embodiment, a proximal portion 390a of rod 390 is translatable with respect to a distal portion 390b thereof. Additionally, proximal portion 390a is proximally biased with respect to distal portion 390b via biasing member 390c (e.g., helical spring). See FIG. 5. Proximal portion 390a includes a pin 391 that is configured to ride along a substantially "L"-shaped slot 391a disposed in first body half 332 (as illustrated in FIG. 5) or second body half 334. Once pin 391 is fully translated distally with respect to slot 391a (i.e., pin 391 moves along a first leg of slot 391a), proximal portion 390a can be rotated about longitudinal axis "A-A" such that pin 391 moves along a second leg of slot 391a, thus preventing proximal translation of proximal portion 390a with respect to distal portion 390b, which releasably locks jaw members 310, 320 in the open position.

While not explicitly illustrated, it is envisioned that one of the first jaw member 310 and the second jaw member 320 is stationary with respect to frame 340. In such an embodiment, lower arm 370 or upper arm 380 would be stationary with respect to frame 340. That is, first cam plate 350 or second cam plate 360 could be omitted from the design or could be configured to not include slots 352 or 362. Further, the orientation of slots 352 or 362 could be configured to limit or otherwise adjust the relative movement between either first cam plate 350 and lower arm 370, or second cam plate 360 and upper arm 380. Additionally, while lower arm 370 and upper arm 380 are illustrated as being curved with respect to the longitudinal axis "A-A," it is envisioned that lower arm 370 and upper arm 380 are co-linear with respect to the longitudinal axis "A-A," e.g., for use with a surgical instrument having linear jaw member (e.g., linear surgical stapling instrument 10a of FIG. 1A or vessel sealing instrument 10c of FIG. 1C).

It is contemplated that the curvature of the first jaw member and second jaw member of the attachable clamp 300 can be adjusted so that the attachable clamp is disposed on the concave side 290 of the jaws 23b or the convex side 291 of the jaws 23b of the surgical apparatus 10b (see FIG. 1B).

Figure 6:
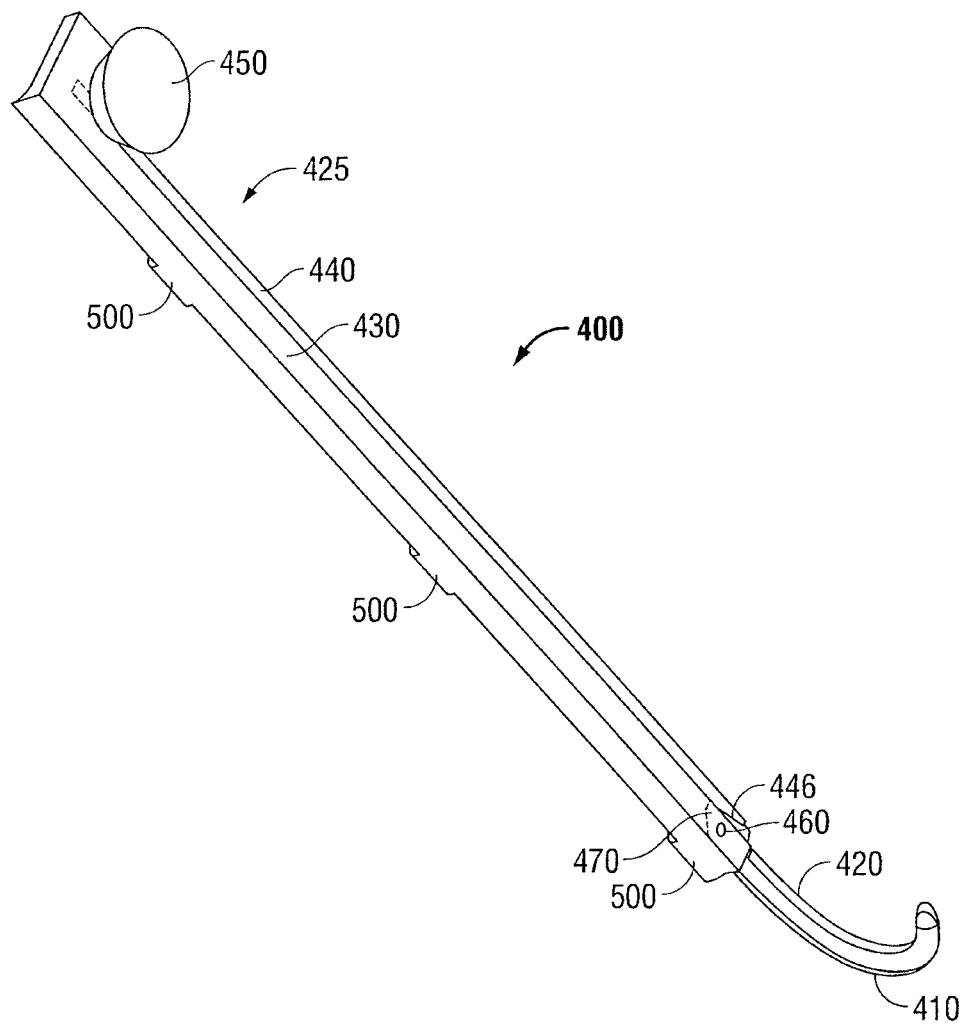
FIG. 6 is a perspective view of an accessory according to a further embodiment of the present disclosure, illustrating a closing mechanism for use with a clamp.
Figure 7:
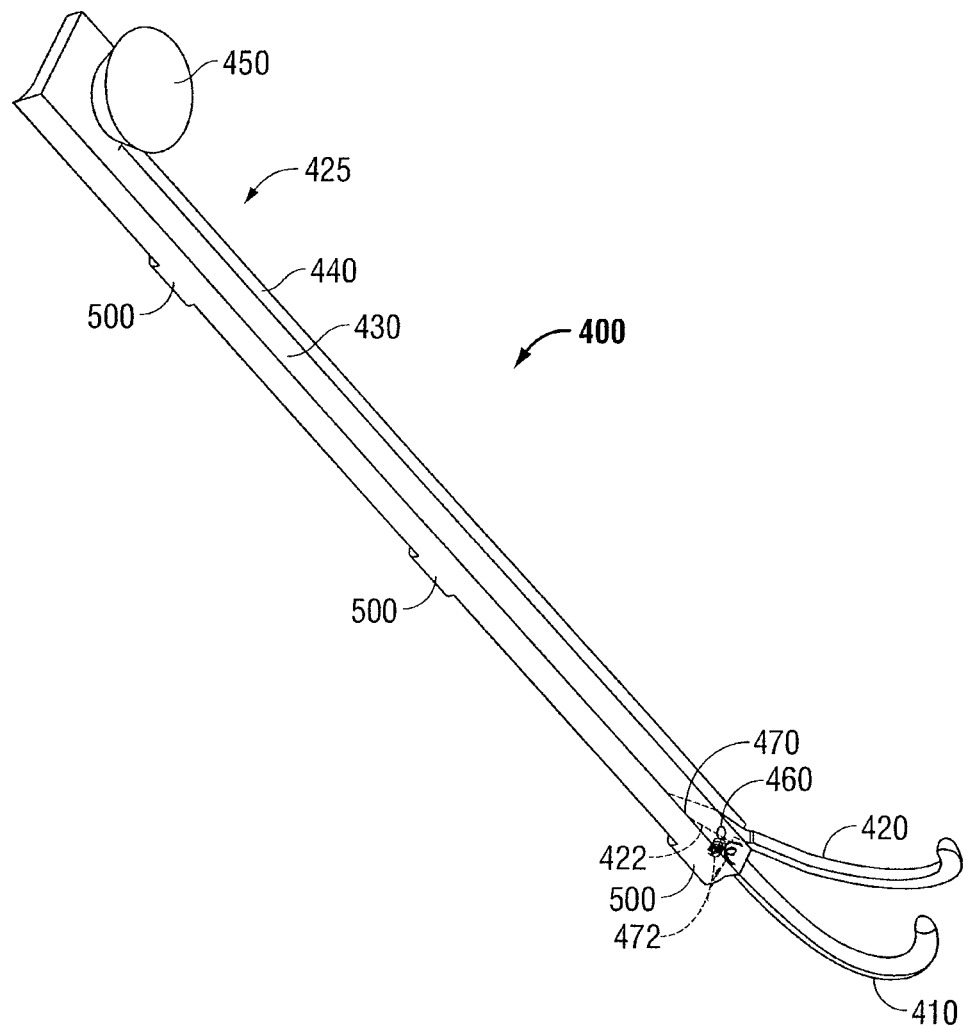
FIG. 7 is a perspective view of the accessory of FIG. 6.
Figure 8:
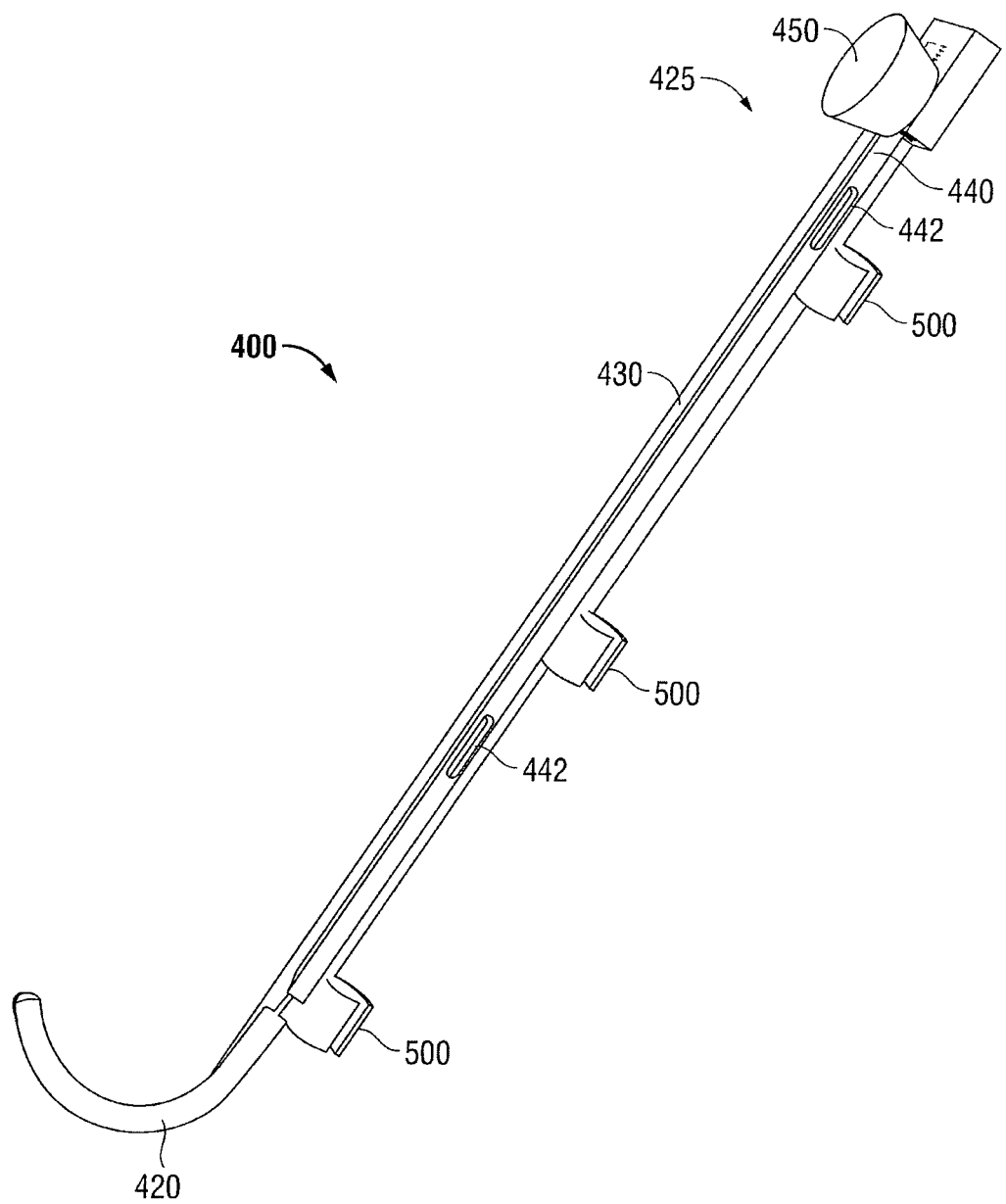
FIG. 8 is a bottom view of the accessory of FIGS. 6-7.

With reference to FIGS. 6-9, another embodiment of an accessory for grasping and/or clamping tissue is shown and is depicted as attachable clamp 400. Attachable clamp 400 includes a first jaw member 410, a second jaw member 420, and an actuation mechanism 425 including a body portion 430, a slide member 440, and a knob 450. In this embodiment, first jaw member 410 and body portion 430 are stationary with respect to each other (and with respect to elongate portion 18 of surgical instrument 10 when attached thereto) and may be monolithically formed with each other. Second jaw member 420 is pivotably disposed with respect to first jaw member 410 and body portion 430 via pivot pin 460 (FIGS. 6 and 7). Pivot pin 460 also extends through a pivot tab 470, as discussed in more detail below. The first jaw member 410 has a tissue contact surface 410a that faces a tissue contact surface 420a on the second jaw member 420.

Pivot tab 470 is disposed adjacent a distal portion of slide member 440 and adjacent a proximal portion of second jaw member 420 (FIGS. 6 and 7). Additionally, pivot tab 470 is fixed to second jaw member 420. It is envisioned that pivot tab 470 is biased via a biasing member 472 (e.g., helical or torsional spring) such that second jaw member 420 is urged towards its open position (FIG. 7).

Figure 9:
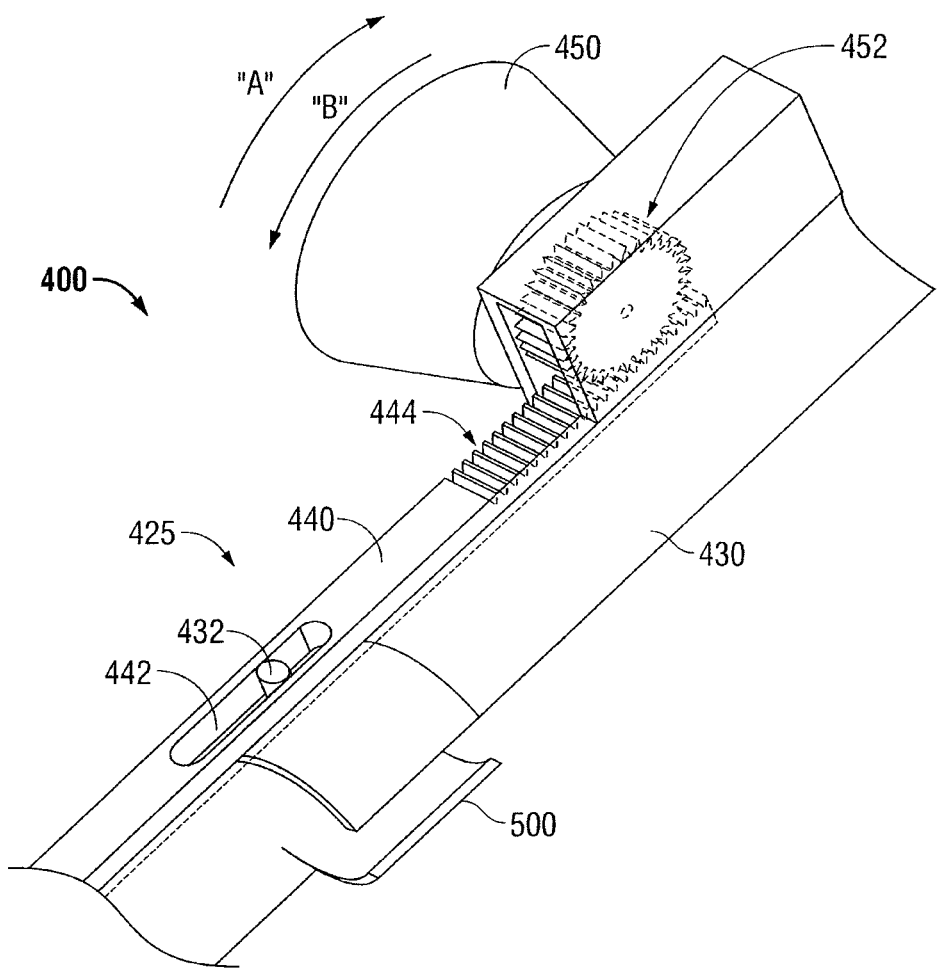
FIG. 9 is another perspective view of the accessory of FIGS. 5-8.

Slide member 440 includes slots 442 therein to accommodate pins 432 of the body portion 430 (see FIG. 9), such that slide member 440 is longitudinally translatable with respect to body portion 430. With particular reference to FIG. 9, a proximal portion of slide member 440 includes a plurality of teeth 444 thereon, which are configured to engage a plurality of teeth 452 of knob 450.

In use, to operate attachable clamp 400, a user rotates knob 450 to pivotably move second jaw member 420 between its open (FIG. 7) and approximated (FIG. 6) positions. More particularly and with specific reference to FIG. 9, rotation of knob 450 in the direction of arrow "A" causes second jaw member 420 to move towards its approximated position. Rotation of knob 450 in the direction of arrow "B" causes second jaw member 420 to move towards its open position. Specifically, upon rotation of knob 450 in the direction of arrow "A," the interaction between teeth 452 of knob 450 and teeth 444 of slide member 440 causes slide member 440 to distally translate such that a distal face 446 (FIG. 6) of slide member 440 engages an approximation surface 422 (FIG. 7) of second jaw member 420, thus causing second jaw member 420 to pivot towards first jaw member 410 against the bias of biasing member 472. Correspondingly, upon rotation of knob 450 in the direction of arrow "B," the interaction between teeth 452 of knob 450 and teeth 444 of slide member 440 causes slide member 440 to proximally translate, thus causing second jaw member 420 to pivot away from first jaw member 410. That is, distal face 446 of slide member 440 moves proximally past approximation surface 422 of second jaw member 420, thus allowing biasing member 472 to return second jaw member 420 to its open position.

Figure 10:
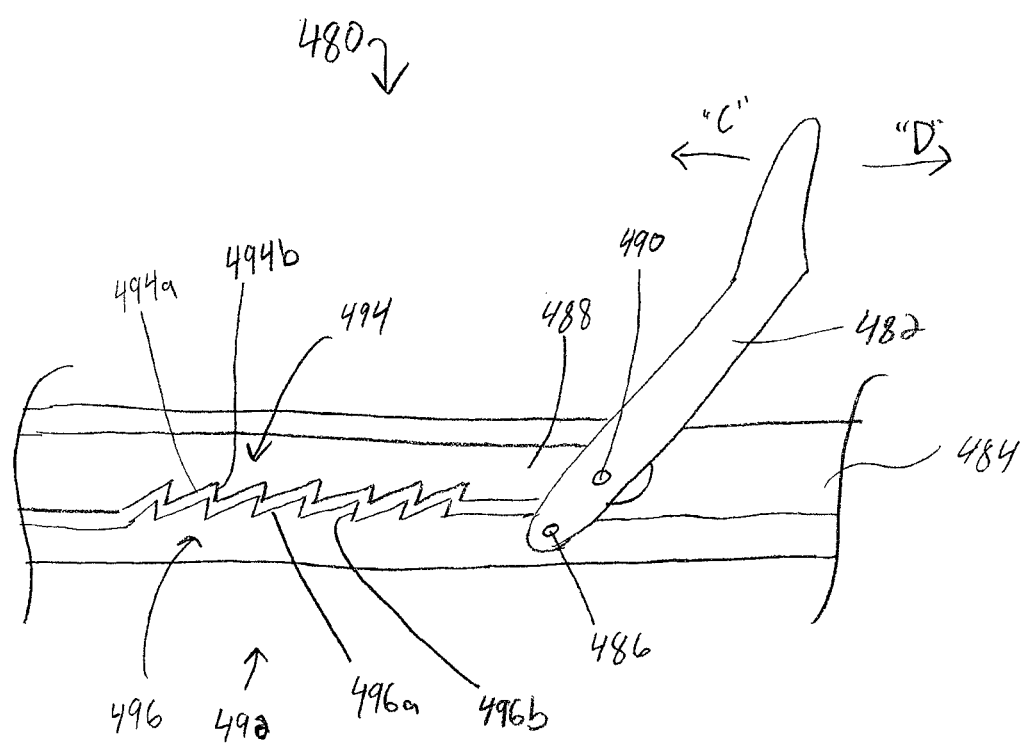
FIG. 10 is a side view of an actuation mechanism according to an embodiment of the present disclosure.

With reference to FIG. 10, another embodiment of an actuation mechanism for use with an accessory of the present disclosure is shown and is depicted as reference number 480. Actuation mechanism 480 includes a cam lever 482 that is pivotably engaged with a body portion 484 of the attachable clamp about pivot pin 486, and pivotably engaged with a slide member 488 of the attachable clamp about pivot pin 490. It is envisioned that body portion 484 is mechanically engaged with a first jaw member of an attachable clamp and that slide member 488 is mechanically engaged with a second jaw member of an attachable clamp.

Certain embodiments of an actuation mechanism include a locking mechanism for holding the jaw members in the approximated position and having an actuator graspable by a user for releasing the actuation mechanism. For example, in FIG. 10, an actuation mechanism having a ratchet mechanism 492 is shown. Ratchet mechanism 492 includes a plurality of teeth 494 disposed on body portion 484 and a plurality of teeth 496 disposed on slide member 488, and is configured to allow controlled and stepped distal advancement of slide member 488 with respect to body portion 484. More particularly, teeth 494 include angled walls 494a and flats or locking member 494b, and teeth 496 include angled walls 496a and flats 496b. As can be appreciated, the interaction between angled walls 494a, 496a and flats 494b, 496b allow movement in the distal direction, but prevent movement in the proximal direction. That is, the flats 494b, 496b maintain slide member 488 in a desired longitudinal position, while restricting the proximal force applied by the compressed tissue.

In use, as cam lever 482 is pushed in the direction of arrow "C," cam lever 482 rotates about pivot pin 486. Pin 490 connects cam lever 482 to slide member 488 such that rotation of cam lever 482 in the direction of arrow "C" distally translates slide member 488 to clamp tissue, for example. Additionally, movement of cam lever 482 in the direction of arrow "D" causes slide member 488 to move proximally with respect to body portion 484, which causes the second jaw member to move towards its open position. Moreover, movement of cam lever 482 in the direction of arrow "D" causes slide member 488 to lift upwardly, thus disengaging teeth 494, 496 and enabling proximal translation of slide member 488 with respect to body portion 484.

Another embodiment of an actuation mechanism including a locking mechanism includes a spring-loaded and shaped recesses, in place of the teeth on slide member 488 and body portion 484 discussed above. The spring-loaded detent is mounted in one of the slide member 488 and body portion 484 and recesses are provided on the other of slide member 488 and body portion 484. The recesses are shaped so that slide member 488 slides in a distal direction, overcoming the detent, but movement of the cam lever 482 in the proximal direction is required to disengage the detent from the recesses and move the slide member 488 in the proximal direction.

The embodiments of an actuation mechanism include a locking mechanism for holding the jaw members in the approximated position and having an actuator graspable by a user for releasing the actuation mechanism discussed above can be used with an attachable clamp having jaw members that are shaped and oriented as shown in FIGS. 1 through 9.

In each of the illustrated embodiments, each attachable clamp 200, 300, 400 is configured to removably engage surgical instrument 10. More particularly, attachable clamp 200 may include one or more attachment members, such as a series of tabs 500, which are configured to clip or slide onto the elongate portion 118 of (and/or a portion of a loading unit configured for use with) the surgical instrument 10. Additionally, it is envisioned that the tabs 500 are removable and/or able to be reoriented (e.g. via screws or the like) to place the tabs 500 on the opposite lateral side of the attachable clamp 200, 300, 400, for example. It is also envisioned that each attachable clamp 200, 300, 400 is attachable to the surgical instrument 10 via other suitable means, such as, for example, screws.

When attachable clamp 200, 300, 400 is used in combination with surgical instrument 10 to compress tissue, it is envisioned that a user may position jaw members 210 and 220, 310, 320, or 410 and 420 of attachable clamp 200, 300, or 400, respectively, about tissue adjacent the location where the tissue will be joined. After the tissue is clamped, and prior to the joining of tissue, the clinician may perform a washout. It is also envisioned that when the jaw members of the attachable clamp are in the approximated position, the user can manipulate (e.g., slightly move) the jaws 23 of the surgical instrument 10.

The present disclosure also relates to a method of using attachable clamp 200, 300, 400 during a surgical procedure. The method includes providing a surgical instrument 10; attaching an attachable clamp to the surgical instrument, the attachable clamp being configured for attachment to the surgical instrument 10; positioning the jaw members of the surgical instrument 10 adjacent tissue; moving at least one jaw member of the attachable clamp from an open position towards an approximated position to engage body tissue; moving at least one of the jaw members of the surgical instrument with respect to the other from an open position towards an approximated position to engage body tissue; and actuating the jaw members of the surgical instrument to join tissue. The method may also include the step of cleansing tissue (e.g., performing a washout) between the steps of moving at least one of the jaw members of the surgical instrument with respect to the other from an open position towards an approximated position to engage body tissue and actuating the jaw members of the surgical instrument to join tissue. For example, in the resection of colonic tissue, the rectum may be washed out while the clamp jaw members are clamped onto the tissue. Then, the surgical stapling instrument (or other instrument for joining tissue) is applied to the section of tissue that has been washed out.

While the above description contains many specifics, these specifics should not be construed as limitations on the scope of the present disclosure, but merely as illustrations of various embodiments thereof. Therefore, the above description should not be construed as limiting, but merely as exemplifications of various embodiments. Those skilled in the art will envision other modifications within the scope and spirit of the disclosure.

The invention claimed is:

1. A surgical stapling instrument and an attachable clamp for use therewith, the attachable clamp comprising:
   a body portion defining a first longitudinal axis and having attachment members configured to attach to an elongate portion of the surgical stapling instrument, the elongate portion of the surgical stapling instrument defining a second longitudinal axis, wherein the first longitudinal axis is spaced laterally from and substantially parallel with the second longitudinal axis;
   a first jaw member extending distally from the body portion and being fixed from longitudinal movement with respect to the body portion;
   a second jaw member extending distally from the body portion, wherein the first jaw member and the second jaw member correspond to jaws of the surgical stapling instrument in shape and orientation; and an actuation mechanism disposed in mechanical cooperation with at least one of the first jaw member and the second jaw member, wherein actuation of the actuation mechanism moves at least one of the first and second jaw members between an approximated position and an open position with respect to the other jaw member;

wherein the attachable clamp is removable from and re-attachable to the surgical stapling instrument.

2. The surgical stapling instrument and attachable clamp of claim 1, wherein the attachment members are configured to removably attach to the body portion and to removably attach to the elongate portion of the surgical stapling instrument.

3. The surgical stapling instrument and attachable clamp of claim 1, wherein each of the first jaw member and the second jaw member are curved with respect to the first longitudinal axis.

4. The surgical stapling instrument and attachable clamp of claim 3, wherein each of the first jaw member and the second jaw member includes a concave side and a convex side.

5. The surgical stapling instrument and attachable clamp of claim 4, wherein the concave sides of the first jaw member and the second jaw member are disposed adjacent the jaws of the surgical stapling instrument.

6. The surgical stapling instrument and attachable clamp of claim 4, wherein the convex sides of the first jaw member and the second jaw member are disposed adjacent the jaws of the surgical stapling instrument.

7. The surgical stapling instrument and attachable clamp of claim 1, wherein the actuation mechanism includes a first cam plate disposed in mechanical cooperation with the first jaw member and disposed in mechanical cooperation with a rod, and wherein translation of the rod causes the first jaw member to move upwardly.

8. The surgical stapling instrument and attachable clamp of claim 7, wherein the actuation mechanism further comprises a second cam plate disposed in mechanical cooperation with the second jaw member and disposed in mechanical cooperation with the rod, wherein translation of the rod causes the second jaw member to move downwardly.

9. The surgical stapling instrument and attachable clamp of claim 8, wherein the translation of the rod in a first direction causes the second jaw member to move downwardly toward the open position.

10. The surgical stapling instrument and attachable clamp of claim 7, wherein the translation of the rod in a first direction causes the first jaw member to move upwardly toward the open position.

11. The surgical stapling instrument and attachable clamp of claim 10, wherein the rod is biased toward a position so that the first jaw member tends to move toward the approximated position.

12. The surgical stapling instrument and attachable clamp of claim 1, wherein the first jaw member and the second jaw member are substantially parallel to one another when the jaw members are in the open and approximated positions.

13. The surgical stapling instrument and attachable clamp of claim 1, wherein the first jaw member is stationary with respect to the body portion.

14. The surgical stapling instrument and attachable clamp of claim 1, wherein the actuation mechanism includes a knob and a slide member, and wherein rotation of the knob causes the second jaw member to pivot towards the first jaw member.

15. The surgical stapling instrument and attachable clamp of claim 14, wherein the knob includes a plurality of teeth which are configured to engage a plurality of teeth of the slide member.

16. The surgical stapling instrument and attachable clamp of claim 1, where a distal portion of the body portion of the clamp is configured to selectively attach to a distal portion of an elongate portion of the surgical stapling instrument.

17. The surgical stapling instrument and attachable clamp of claim 16, wherein a proximal portion of the body portion of the clamp is configured to selectively attach to a proximal portion of the elongate portion of the surgical stapling instrument.

18. The surgical stapling instrument and attachable clamp of claim 1, wherein the body portion is configured to selectively attach to a lateral side of an elongate portion of the surgical stapling instrument.

19. The surgical stapling instrument and attachable clamp of claim 1, wherein the elongated portion of the surgical stapling instrument is parallel with the body portion of the attachable clamp along an entire length of the body portion.

20. The surgical stapling instrument and attachable clamp of claim 1, wherein a proximal-most end of the attachable clamp is configured to longitudinally align with the elongate portion of the surgical stapling instrument when the attachable clamp is engaged with the surgical stapling instrument.

21. A surgical stapling instrument and an attachable clamp for use therewith, the attachable clamp comprising:
a body portion defining a first longitudinal axis and having attachment members configured to attach to the surgical stapling instrument, at least one attachment member disposed adjacent a distal portion of the body portion and configured to attach to a distal portion of an elongate portion of the surgical stapling instrument;
a first jaw member extending distally from the body portion and being fixed from longitudinal movement with respect to the body portion;
a second jaw member extending distally from the body portion, wherein the first jaw member and the second jaw member correspond to jaws of the surgical stapling instrument in shape and orientation; and
an actuation mechanism disposed in mechanical cooperation with at least one of the first jaw member and the second jaw member, wherein actuation of the actuation mechanism moves at least one of the first and second jaw members between an approximated position for clamping tissue and an open position with respect to the other jaw member, the actuation mechanism holding the jaw members in the approximated position and having an actuator graspable by a user for releasing the actuation mechanism;
wherein the attachable clamp is removable from and re-attachable to the surgical stapling instrument.

22. The surgical stapling instrument and attachable clamp of claim 21, wherein the attachment members are configured to removably attach to the elongate portion of the surgical stapling instrument.

23. The surgical stapling instrument and attachable clamp of claim 21, wherein the actuation mechanism includes a first cam plate disposed in mechanical cooperation with the first jaw member and disposed in mechanical cooperation with a rod, and wherein translation of the rod causes the first jaw member to move upwardly toward the open position.

24. The surgical stapling instrument and attachable clamp of claim 21, wherein the actuation mechanism biases the first jaw member and the second jaw member toward the approximated position.

25. The surgical stapling instrument and attachable clamp of claim 21, wherein the first jaw member and the second jaw member are substantially parallel to one another when the jaw members are in the open and approximated positions.

26. The surgical stapling instrument and attachable clamp of claim 21, wherein the first jaw member is stationary with respect to the body potion.

27. The surgical stapling instrument and attachable clamp of claim 21, wherein a proximal portion of the body portion of the clamp is configured to selectively attach to a proximal portion of the elongate portion of the surgical stapling instrument.

28. The surgical stapling instrument and attachable clamp of claim 21, wherein the elongate portion of the surgical stapling instrument defines a second longitudinal axis, and wherein the first longitudinal axis is spaced laterally from and substantially parallel with the second longitudinal axis.

29. The surgical stapling instrument and attachable clamp of claim 21, wherein the body portion of the clamp is fixed from longitudinal movement with respect to the elongate portion of the surgical stapling instrument when the attachable clamp is engaged with the surgical stapling instrument.

30. The surgical stapling instrument and attachable clamp of claim 21, wherein the elongated portion of the surgical stapling instrument is parallel with the body portion of the attachable clamp along an entire length of the body portion.

31. The surgical stapling instrument and attachable clamp of claim 21, wherein a proximal-most end of the attachable clamp is configured to longitudinally align with the elongate portion of the surgical stapling instrument when the attachable clamp is engaged with the surgical stapling instrument.

32. The surgical stapling instrument and attachable clamp of claim 21, wherein each of the first jaw member and the second jaw member are curved with respect to the longitudinal axis.

* * * * *